United States Patent [19]

Leonard

[11] 4,234,308
[45] Nov. 18, 1980

[54] DEVICE FOR LOCKING A TOOL IN A DENTAL HANDPIECE

[75] Inventor: Henri Leonard, Besancon, France

[73] Assignee: Micro-Mega S.A., Besancon, France

[21] Appl. No.: 898,022

[22] Filed: Apr. 20, 1978

[30] Foreign Application Priority Data

Jun. 7, 1977 [FR] France ................................ 77 17974

[51] Int. Cl.³ .............................................. A61C 1/14
[52] U.S. Cl. .................................................... 433/127
[58] Field of Search ............................. 32/27; 433/127

[56] References Cited

U.S. PATENT DOCUMENTS

| 462,896 | 11/1891 | Eddy | 32/27 |
|---|---|---|---|
| 870,825 | 11/1907 | Hardy | 32/27 |
| 1,688,136 | 10/1928 | Chayes et al. | 32/27 |
| 2,010,421 | 8/1935 | Terry | 32/27 |
| 2,231,969 | 2/1941 | Tifft | 32/27 |
| 2,591,772 | 4/1952 | Bjorklund | 32/27 |
| 2,726,449 | 12/1955 | Tirocchi | 32/27 |
| 3,499,223 | 3/1970 | Lieb et al. | 32/27 |
| 3,909,946 | 10/1975 | Watanabe | 32/27 |

FOREIGN PATENT DOCUMENTS 743771  11/1943  Fed. Rep. of Germany ............. 32/27

Primary Examiner—Louis G. Mancene
Assistant Examiner—John J. Wilson
Attorney, Agent, or Firm—Robert E. Burns; Emmanuel J. Lobato; Bruce L. Adams

[57] ABSTRACT

This device for locking a dental tool in a handpiece of the contra-angle type comprises a keeper plate slidably mounted on the external surface of the holder and rigidly associated with a control member formed with a thumb-piece consisting of an inclined surface portion thereof. A keyhole formed in the keeper plate is engaged by a suitable shaped end portion of the tool shank so that when the keeper plate is moved to its release position the tool shank can pass through the larger portion of the keyhole and when the plate is in its locking position to which it is urged by a return spring the end portion of the tool shank engages the narrow portion of the keyhole.

1 Claim, 4 Drawing Figures

DEVICE FOR LOCKING A TOOL IN A DENTAL HANDPIECE

FIELD OF THE INVENTION

This invention relates to means for locking a dental tool in the head of a dental tool holder or handpiece of the contra-angle type comprising a plate adapted to slide on the body of the contra-angle and provided with an elongated aperture formed at one end with a bore of a diameter greater than the width of said aperture, the latter being adapted to co-act with a groove formed in the shank of the tool, e.g. a boring tool, said plate being movable from a locking position in which the tool groove engages said elongated aperture to a release position in which said groove is disengaged from said elongated aperture and the tool can escape through said bore having a diameter greater than the width of said aperture.

REFERENCE TO THE PRIOR ART

Devices of the type broadly described hereinabove are already known wherein the lock plate must be pushed towards the head end when it is desired to release the tool. This arrangement is objectionable in that it is awkward to handle. It is the essential object of the present invention to avoid this inconvenience.

DESCRIPTION OF THE INVENTION

For this purpose, the device according to the present invention is characterized in that the sliding plate, in its locking position, lies at the front of the holder and is rigid with a control member responsive to a return spring urging said control member to its locking position, said control member being provided on its outer surface with a thumb-piece inclined forwardly and inwardly of the holder, whereby said control member can be pulled backwards in relation to the holder for moving said plate to its release position.

Due to the provision of this inclined thumb-piece, the control member has a shape more consistent with the configuration of the oblique arm of the contra-angle. Besides, with this arrangement the actuation of the locking device is greatly facilitated since it is easier to pull the control member for releasing the dental tool than pushing this member, the practician's thumb engaging quite naturally the inclined surface portion of the control member.

A clearer understanding of the present invention will be had if reference is made to the following description given with reference to a typical form of embodiment of the invention which is illustrated in the accompanying drawing.

DESCRIPTION OF THE PREFERRED EMBODIMENT

Figure 1:
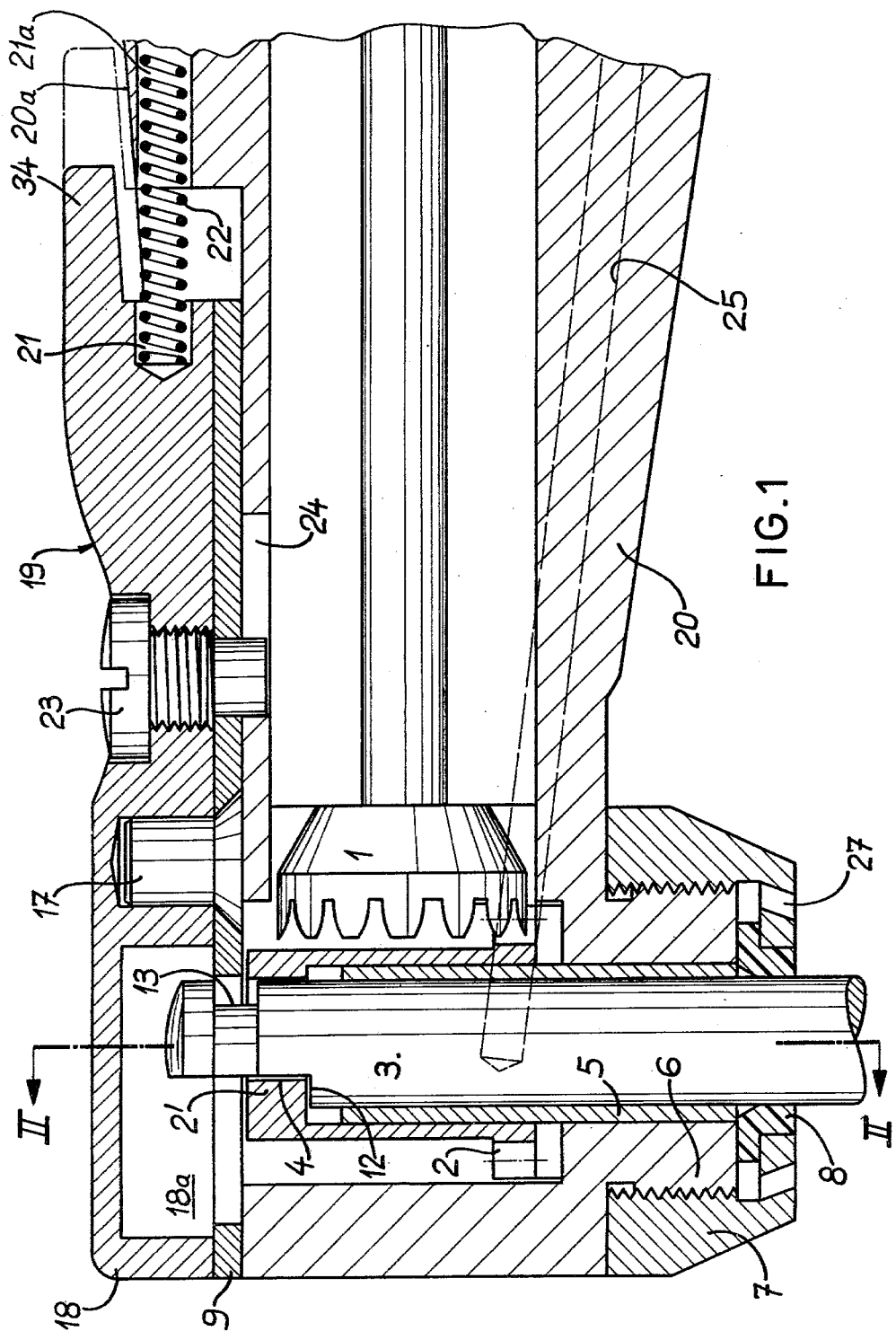
FIG. 1 is a diagrammatic sectional view of a contra-angle provided with the locking device according to this invention.

Mounted in the body 20 of the contra-angle is a gear comprising a pinion 1 in constant meshing engagement with a hollow pinion 2 disposed at right angles to pinion 1 and driving in turn the dental tool 3, for example a milling cutter, by means of a flat face 4. The hollow pinion 2 is rotatably mounted on a hollow shaft 5 acting as a bearing to the tool 3 driven in turn in a support or head 6 formed integrally at the end of said body 20: this head 6 comprising a screw-threaded portion engaged by a ring nut 7 for holding in position a flanged seal 8.

Figure 3:
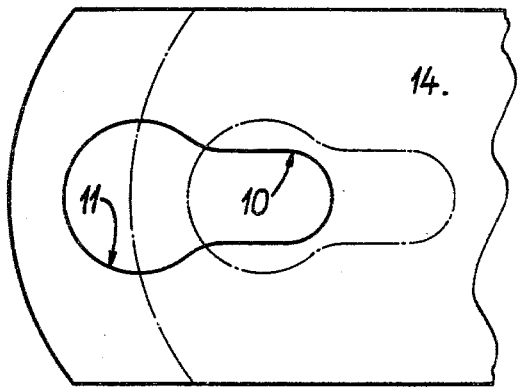
FIG. 3 is a fragmentary plane view of the locking plate.
Figure 4:
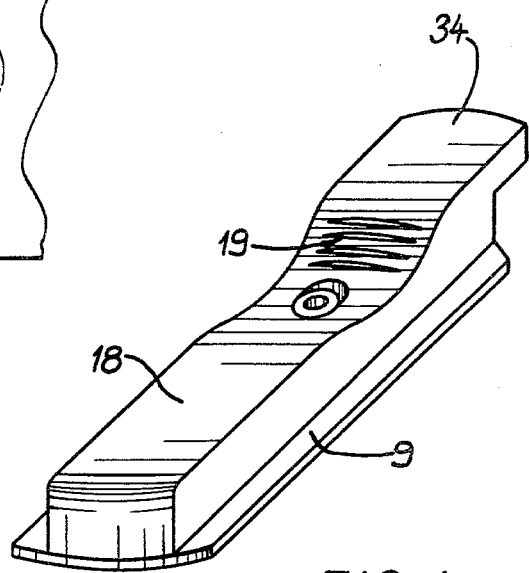
FIG. 4 is a perspective view of the locking assembly.
Figure 2:
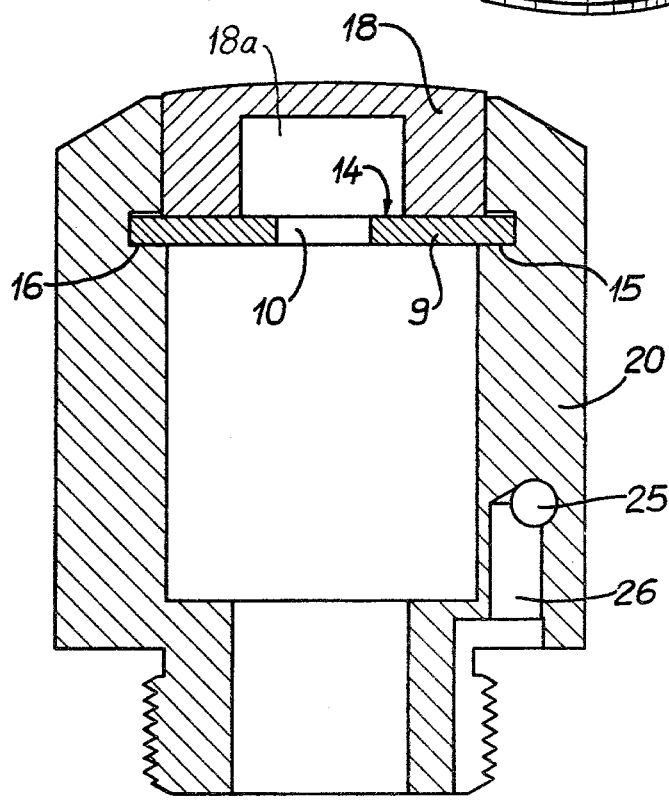
FIG. 2 is a section taken along the line II—II of FIG. 1.

The tool 3 is retained longitudinally in the hollow shaft 5 by means of a keeper plate 9 in which an elongated aperture 10 is formed: this aperture 10 comprises at its end adjacent the free end of the contra-angle, a bore 11 a portion having a diameter greater than the width of the elongated aperture 10, as clearly shown in FIG. 3. The longitudinal play of tool 3 is limited on the one hand by the engagement of a shoulder formed by a milled portion 12 with the wall 2' of hollow pinion 2 and on the other hand by the upper wall of a groove 13 formed in the shank of said tool adjacent the inner end thereof, this upper wall engaging the top face 14 of keeper plate 9. In addition, this plate 9 is slidably mounted in corresponding lateral grooves 15, 16 formed in the body 20 of the tool holder (FIG. 2).

The keeper plate 9 is secured by means of a screw 17 to an elongated control member 18 provided in a forward end portion a downwardly opening recess 18a, on the upper side adjacent the handle of the contra-angle, with a surface 19 inclined forwardly and inwardly. On the other hand, this control member 18 is provided at its rear end with a blind hole 21 housing one end of a coil compression spring 22 the opposite end of which is housed in a cavity formed in an upward projection 20a of the body 20. A screw 23 extending through the control member 18 and keeper plate 9 has a stud end of reduced diameter engaged in an elongated aperture 24 formed in the tool holder body 20 and acts as a stop for limiting the longitudinal movements of keeper plate 9 and control member 18 with respect to the body 20.

To introduce the tool 3 into the contra-angle holder head 6 the user pulls the control member 18 by exerting a backward pressure with his thumb on the inclined surface 19, against the force of spring 22, so that the keeper plate can be moved to the right as seen in FIG. 1, i.e. to the position shown in dash and dot lines in FIG. 3. Thus, the bore 11 having a diameter greater than the inner end of tool 3 registers with this tool end and the latter can be introduced into the bore 11. By releasing the control member 18 the latter urged by spring 22 resumes its initial position shown in FIG. 1, the groove 13 co-acting at this time with the elongated aperture 10 of keeper plate 9: the accurate positioning of tool 3 is obtained by causing its milled portion 12 to engage the wall 12' of hollow pinion 2. Since the width of the elongated aperture 10 formed in plate 9 is slightly greater than the thickness of the tool 3 at the level of its groove 13 and smaller than the diameter of the tool shank, the tool is held against axial movement in the head but can be rotatably driven through pinion 2 and flat face 4.

The rear end of control member 18 comprises an extension 24 which, in the release position, covers or overlaps with a certain clearance the body 20 of the hand tool holder. The body 20 is also provided, of course, with an internal longitudinal passage 25 opening into a hole 26 formed in the head 6 of the hand tool holder and communicating in turn with orifices 27 having their outlets directed towards the operating end of tool 3 for supplying cooling fluid thereto.

What is claimed is:

1. A dental handpiece of contra-angle type comprising a housing including a head for receiving a tool having a shank with a groove near the end of the shank, means in said housing for driving said tool, said housing having in its upper portion an opening through which said grooved shank end of a tool extends, and longitudinally extending grooves on opposite sides of said opening, means for locking a tool in said handpiece comprising an elongate flat locking plate slidable lengthwise in said longitudinally extending grooves of said housing and having in a forward end portion a key-hole opening having a forward portion of a size to receive the shank of a tool and an elongate rearward portion engageable in said groove in the shank of a tool to retain the tool in said handpiece, an elongate control member overlying and fixed to said locking plate, said control member having in a forward end portion a downwardly opening recess overlying said opening of said locking plate, and a rear end portion which is thicker than said forward end portion, and has an upper surface between said forward end portion and rear end portion which is inclined rearwardly and upwardly, said housing having an upward projection rearwardly of said control member, and said upward projection of the housing and the rear end of said control member having aligned longitudinally extending bores, a compression spring received in said bores and acting between said control member and said upward projection of the housing to urge said control member and locking plate forwardly to bring said elongate portion of said opening in the locking plate into engagement with said groove of the shank of a tool received in said head to retain said tool, and means for limiting longitudinal movement of said locking plate and control member relative to said housing, said locking plate being moveable rearwardly against the action of said spring to release a tool by digital pressure on said upwardly and rearwardly inclined surface of said control member, said control member having a rearwardly extending tail portion which overlies and thereby covers said spring and, in a rearward position of said control member, overlies said upward projection of the housing, and said means for limiting longitudinal movement of said locking plate and control member comprising a screw extending through a threaded hole in a mid-portion of said control member and having an inner end portion extending into an elongate recess of limited length in the upper surface of said housing, whereby said locking plate, control member and spring are assembled on said housing by sliding said locking plate in said grooves, positioning said spring in said bores, moving said locking plate and control member rearwardly to compress said spring, and screwing said screw inwardly to engage its inner end in said recess of the housing, whereupon said screw serves the dual function of limiting longitudinal movement of said locking plate and of retaining said locking plate, control member and spring assembled with said housing.

* * * * *